(12) United States Patent
Rubin

(10) Patent No.: US 7,488,703 B2
(45) Date of Patent: *Feb. 10, 2009

(54) SYSTEM AND METHOD FOR A FRAGRANT POLYMER CONFIGURED FOR USE IN A GROWING MEDIUM

(75) Inventor: Patti Donner Rubin, 19500 Turnberry Way, Aventura, FL (US) 33180

(73) Assignee: Patti Donner Rubin, Aventura, FL (US)

( * ) Notice: Subject to any disclaimer, the term of this patent is extended or adjusted under 35 U.S.C. 154(b) by 832 days.

This patent is subject to a terminal disclaimer.

(21) Appl. No.: 10/959,378

(22) Filed: Oct. 6, 2004

(65) Prior Publication Data

US 2006/0074006 A1 Apr. 6, 2006

(51) Int. Cl.
*C09K 17/14* (2006.01)
*A01N 25/28* (2006.01)
*A01G 9/10* (2006.01)
*A01G 31/00* (2006.01)

(52) U.S. Cl. .................. 504/359; 504/358; 504/360; 504/362; 504/366; 504/367; 47/59 R; 47/59 S; 47/58.1 SC; 512/4

(58) Field of Classification Search .............. 512/4
See application file for complete search history.

(56) References Cited

U.S. PATENT DOCUMENTS

| 4,051,628 | A | * | 10/1977 | Knapp et al. ............... 47/48.5 |
| 4,128,508 | A | * | 12/1978 | Munden ...................... 512/1 |
| 4,351,754 | A | * | 9/1982 | Dupre ........................ 524/445 |
| 5,382,270 | A | * | 1/1995 | Graham et al. ............. 47/62 N |
| 5,477,640 | A | * | 12/1995 | Holtkamp, Jr. ............. 47/66.6 |
| 6,013,524 | A | * | 1/2000 | Friars et al. ................ 435/420 |
| 6,624,136 | B2 |  | 9/2003 | Guerin et al. |
| 6,793,915 | B1 | * | 9/2004 | Guenin et al. .............. 424/65 |
| 7,311,900 | B2 | * | 12/2007 | Conover .................. 424/76.1 |
| 2001/0030243 | A1 | * | 10/2001 | Hurry et al. ................ 239/60 |
| 2002/0041860 | A1 | * | 4/2002 | Requejo .................... 424/76.1 |
| 2003/0065087 | A1 | * | 4/2003 | Nambu et al. ............. 524/588 |

FOREIGN PATENT DOCUMENTS

CA 1328744 4/1994

* cited by examiner

*Primary Examiner*—Joseph D Anthony
(74) *Attorney, Agent, or Firm*—Bryan G. Pratt; Rader, Fishman & Grauer PLLC

(57) ABSTRACT

A fragrant polymer configured to be associated with a growing medium includes a water absorbent polymer, and a fragrance agent encapsulated in the water absorbent polymer. Encapsulating a fragrance agent in an absorbent polymer allows for systematic release of the fragrance agent, thereby reducing the effect of foreign odors that often accompany potted plants.

12 Claims, 4 Drawing Sheets

US 7,488,703 B2

SYSTEM AND METHOD FOR A FRAGRANT POLYMER CONFIGURED FOR USE IN A GROWING MEDIUM

BACKGROUND

Homes, offices, and other indoor areas have traditionally been decorated with potted plants, such as trees, shrubs, and flowers, to produce warm and inviting atmospheres or to make the indoor areas feel more "natural." Additionally, the inclusion of potted plants in indoor areas has been shown to increase the amount of useable oxygen. Unfortunately, the creation of a natural ambience through the use of potted plants is often accompanied by foreign or earthy smells that emanate from the potting soil or other organic material used to pot the plants. When maintained indoors, the foreign or earthy smells can be undesirable and can negate the visually aesthetic benefits of decorating an indoor area with potted plants.

A number of methods have been used to eliminate or reduce the effects of the foreign or earthy smells that traditionally accompany potted plants. Current methods include spraying a room with perfumes and/or deodorizers. Additionally, another traditional method for reducing the effects of undesirable smells being emanated by a potted plant includes using scented candles in the affected room. Further solutions have included the introduction of fragrance packets or other scented items placed in various locations throughout an affected room. These traditional methods, however, require constant attention to maintain a pleasant aroma because they typically do not have long-lasting effects. Rather, the aromas produced by traditional methods typically fade within a few hours, requiring a user to then refresh the scent, such as by spraying the room again or lighting another candle. Furthermore, the above-mentioned traditional odor negating methods do not eliminate the foreign or earthy smells, rather they add smells to the room, thereby temporarily masking the undesirable foreign or earthy smells.

SUMMARY

A fragrant polymer configured to be associated with a growing medium includes a water absorbent polymer, and a fragrance agent encapsulated in the water absorbent polymer.

According to one exemplary embodiment, a fragrant polymer is configured to be associated with a growing medium. The exemplary fragrant polymer includes from about 70.0% to about 99.9% water absorbent polymer, and from about 0.1% to about 30.0% or more by weight fragrance agent encapsulated in the water absorbent polymer. According to this exemplary embodiment, the water absorbent polymer is configured to systematically release the fragrance agent.

Additionally, a method of making a fragrant potting soil includes adding a fragrant polymer including a fragrance agent to a potting medium, wherein the fragrant polymer is configured to systematically release the fragrance agent.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

Figure 1:
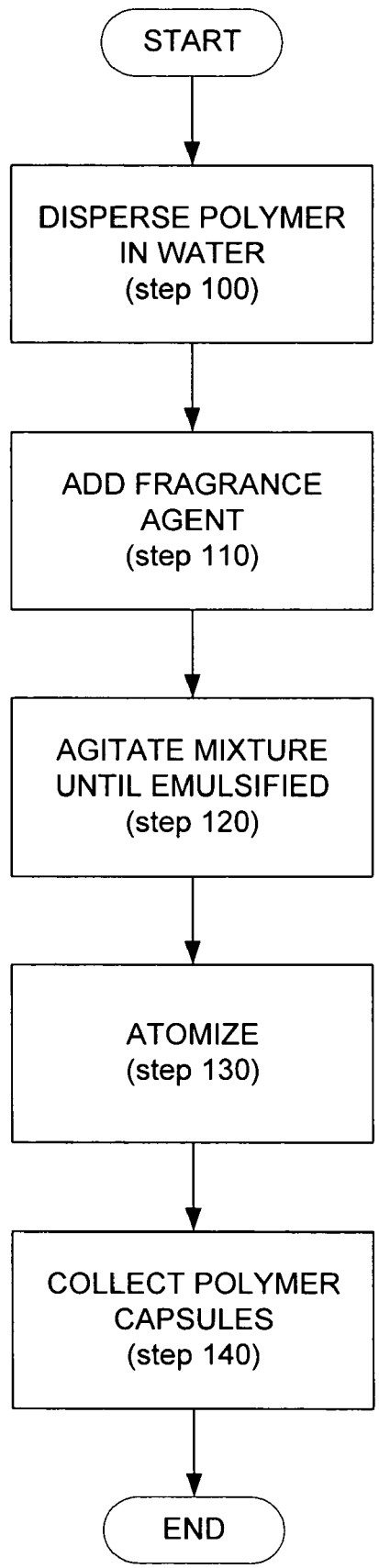
FIG. 1 is a simple block diagram illustrating a method of forming a fragrant polymer configured to be used in a growing medium, according to one exemplary embodiment.

The following description includes specific details in order to provide a thorough understanding of the novel fragrant polymer configured to be incorporated into any growing medium. The skilled artisan will understand, however, that the products and methods described below can be practiced without employing these specific details. Indeed, they can be modified and can be used in conjunction with additional products and techniques known to those of skill in the art.

In order to eliminate the foreign earthy odors that often emanate from potting soils or other growing mediums, or to freshen an area by providing a desired smell or aroma, the present system and method discloses a fragrant polymer configured to be incorporated with any traditional growing medium. According to one exemplary embodiment, the fragrant polymer is configured to release a fragrance agent when water is added to the polymers, thereby creating a pleasant aroma rather than a foreign earthy fragrance traditionally associated with potable growing mediums. Accordingly, the fragrant polymer includes at least two components: a fragrance agent and an encapsulating polymer.

According to one exemplary embodiment, polymers suitable for use as the fragrant polymer capsule comprise any polymer that can be used with or added to a growing medium including, but not limited to, a wide variety of anionic, cationic, and nonionic materials. Suitable polymers include, but are in no way limited to, acrylic polymers such as acrylamides, acrylates, and co-polymers thereof; poly(alkylene oxides) such as poly(ethylene oxide); cross-linked polyethylene oxide co-polyurethane hydrogel; polyvinyl alcohols; ethylene maleic anhydride copolymer; polyvinylethers; polyacrylic acids; polyvinylpyrrolidones; polyvinylmorpholines; polyamines; polyethyleneimines; polyquaternary ammoniums; saponified copolymers of vinyl acetate-acrylic acid ester; and hydrolyzed copolymers of acrylonitrile or acrylamide, or crosslinked polymers of these hydrolyzed copolymers; partially-neutralized crosslinked poly(acrylic acid); natural based polysaccharide polymers such as methyl celluloses, carboxymethyl celluloses, carboxymethyl starches, hydroxypropyl celluloses, algins, alginates, carrageenans, acrylic grafted starches, acrylic grafted celluloses, chitin, chitosan, starch-acrylonitrile, neutralized graft polymers of starch-acrylic acid; and synthetic polypeptides such as polyaspartic acid, polyglutamic acid, polyasparagins, polyglutamines, polylysines, and polyarginines; as well as the salts, copolymers, cross-linked derivatives and mixtures of any of the foregoing polymers. The polymers may be hydrophilic (water soluble) or hydrophobic (water insoluble) according to various embodiments. Cross-linking hydrophilic polymers can increase the insolubility of the cross-linked compound. Additionally, cross-linked compounds have the capability of absorbing great amounts of water.

In one exemplary embodiment the polymer capsule of the present fragrant polymer is made from a potassium- or sodium-based polymer, such as a synthetic polyacrylate/polyacrylamide copolymer. Like many absorbent polymers, synthetic polyacrylate/polyacrylamide copolymer can absorb many hundred times its weight in water, thereby adding water retention capabilities to any growing medium containing the present fragrant polymer. In another exemplary embodiment, the absorbent polymer capsule is acrylamide/potassium acrylate copolymer. Potassium-based polymers are non-toxic and do not cause harm to the environment. Additionally, potassium is a nutrient that promotes plant development.

The polymer capsule carries a fragrance agent that can be released to the environment to create a pleasant aroma, as mentioned previously. The aromas that can be produced by the fragrance agent include, but are in no way limited to, food, vegetable, fruit, plant, floral, spice, and natural environment aromas. Examples of the above-mentioned aromas include, but are not limited to, camphoraceous, anise, balsam, caramel, chocolate, cinnamon, honey, citrus, butter, cheese, cream, banana flower, blueberry, carnation, gardenia, geranium, hawthorn, hibiscus, honeydew, hyacinth, iris, jasmine, jonquil, lilac, lily, magnolia, marigold, narcissus, orchid, rose, violet, apple, apricot, banana, berry, cantaloupe, cherry, black cherry, coconut, golden apple, grape, grapefruit, lemon, lime, mango, jam, melon, peach, pear, pineapple, plum, quince, raspberry, strawberry, watermelon, caraway, sage, mint, nut, hazelnut, almond, peanut, walnut, pistachio, smoke, citronella, cucumber, onion, garlic, green, herbaceous, woody, bamboo, pine, evergreen, Russian olive, cedar, lemon tree, lemongrass, mossy, herbal moss, pepper, potpourri, vanilla, French vanilla, cedar wood vanilla, coffee, earthy, wine, baby powder, baked apple, bread, cake, cookie, clover, lavender, rainwater, seaside, tropical rain, buttered rum, blueberry muffin, cappuccino brulee, tea, carrot cake, cherry cobbler, cinnamon roll, lemon chiffon, mulberry, pumpkin, pumpkin pie, pumpkin spice, smores, strawberry rhubarb pie, pumpkin nectarine, vanilla lavender, mulled wine, green tea, pomegranate, sandalwood, mandarin cassis, freesia, honeysuckle, herbs of province, sea water, and combinations of any of the above.

A fragrance agent encapsulated within the polymer provides the above-mentioned aromas. Suitable fragrance agents include, but are not limited to, essential oils; fixed oils; resins or resinoids; oleoresins, absolutes and concretes; fragrance chemicals; and floral water. Essential oils refer to any volatile aromatic liquid essence that is extracted by steam, distillation, expression or solvent extraction from aromatic plants such as flowers, grasses, fruits, leaves, roots, and/or trees. Fragrance chemicals may include, but are in no way limited to, synthetic odoriferous chemicals, complex compositions obtained using many odoriferous products as a mixture, and/or excipient products which ensure homogeneity of the fragrance chemical. Fragrance chemicals include, but are not limited to, products that may be aliphatic or aromatic ketones; aliphatic or aromatic aldehydes; condensation products of aldehydes and amines; aromatic or aliphatic lactones; aromatic or aliphatic ethers or esters; aliphatic alcohols of varied molecular mass; linear, cyclic, or aromatic saturated or unsaturated hydrocarbons; and terpenes, which may or may not be polynuclear. In one exemplary embodiment, the fragrance agents incorporated in the present system and method are isotropic and hydrophobic compounds. The solubility of the exemplary isotropic and hydrophobic compounds in water at pH 7 typically does not exceed 10% by weight, according to one exemplary embodiment.

In one alternative exemplary embodiment, the fragrance agent comprises an agent configured to repel insects. According to one exemplary embodiment, the fragrance agent includes citronella, which repels various specific insects including mosquitoes, black flies, fleas, and ticks, as well as dogs and cats. Alternatively, the fragrance agent includes a nicotine scent that repels insects such as mealy bugs. In other embodiments, a pesticide or insecticide may also be encapsulated inside the polymer capsule in addition to, or instead of, the fragrance agent. When used in conjunction with the potting media as described below, the pesticide or insecticide can detract rodents, insects, and other undesirable organisms from eating or destroying the plant and/or the growing medium surrounding the plants.

The concentration of the fragrance agent can be 100% concentrated or alternatively, the fragrance agent may be diluted with water or an organic solvent. According to one exemplary embodiment, the fragrance agent typically ranges from about 0.01% to about 99.9% by weight of the fragrant polymer. In another embodiment, the fragrant agent ranges from about 0.1% to about 30.0% by weight of the fragrant polymer. In yet another embodiment the fragrant agent ranges from about 10% to about 20% by weight of the fragrant polymer. Essentially any range of fragrant agent may be included, depending on the capabilities of the polymer.

Generally the fragrant polymer comprises one or more polymer capsules in which the fragrance agent inside the capsule is a solid, liquid, or gas. The fragrant polymers are typically prepared by microencapsulation techniques known to those of skill in the art. Appropriate microencapsulation processes include both physical and chemical techniques, as will be described in further detail below.

Physical methods use commercially available equipment to create and stabilize the capsules. In one exemplary embodiment, the microencapsulation is performed by a spray-drying method, as illustrated in FIG. 1. Generally, the spray drying process begins by creating an emulsion of the capsule polymer and fragrance agent. In one embodiment, as shown in FIG. 1, the emulsion is made by dispersing or dissolving the capsule polymers in a liquid solution such as water (step 100). Once the polymer has been dispersed or dissolved in a solution, the fragrance agent is slowly added (step 110) and the mixture is rapidly agitated until such time as emulsification is complete (step 120).

Once an emulsion has been created, the liquid emulsion is atomized (step 130) into a heated air stream supplied to a drying chamber. The spray-drying process uses a two-nozzle (internal or external mix) assembly, allowing the heated air from an annular geometry to atomize and implode the issuing liquid stream to form fine polymer capsules carrying the microencapsulated fragrance agent in a dispersed state, according to one exemplary embodiment. These atomized particles assume a somewhat spherical shape as they fall through the gaseous medium, and the fragrance agent is encased in the aqueous phase. With high particle-specific surface areas, heat from the drying chamber flash-evaporates the solvent or aqueous media, rendering the polymer capsules cyclone-collected into a holding chamber (step 140).

Figure 2:
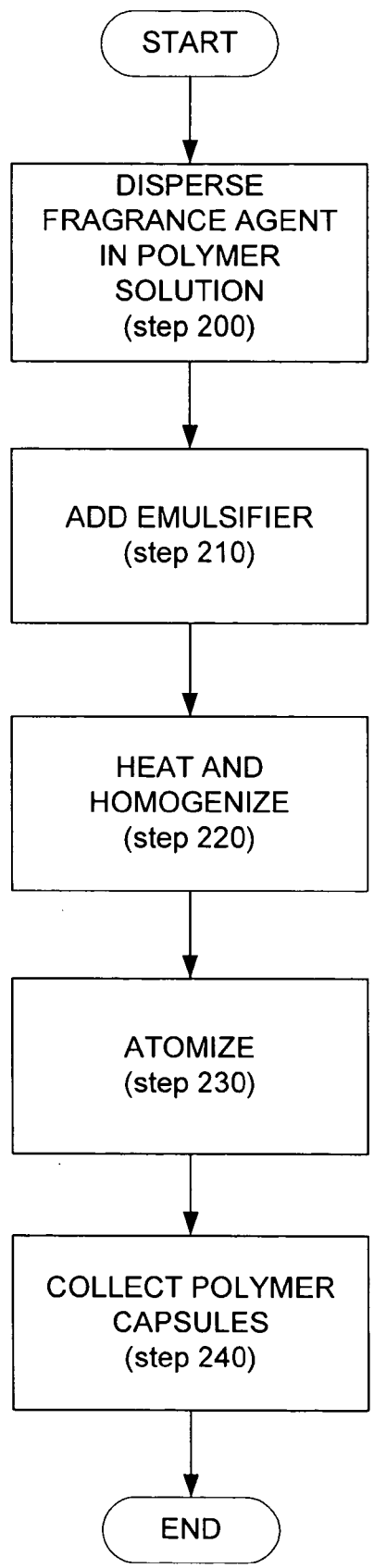
FIG. 2 is a simple block diagram depicting a method of forming a fragrant polymer for use in a growing medium, according to one exemplary embodiment.

In another embodiment, as shown in FIG. 2, the emulsion is made by dispersing the fragrance agent in a polymer solution containing the polymer capsule material to create a dispersion (step 200). An emulsifier is then added to the dispersion (step 210) and the dispersion is then heated and homogenized (step 220). This homogenization creates an oil-in-water type of emulsion. Additionally, a cross-linking agent may be added to the emulsion(s) to enhance the water absorbing ability of the resulting capsule. Once the emulsion has been created, the liquid emulsion is atomized (step 230), as is known in the art, to form polymer capsules. The polymer capsules are then collected (step 240) for use in a growing medium.

Figure 3:
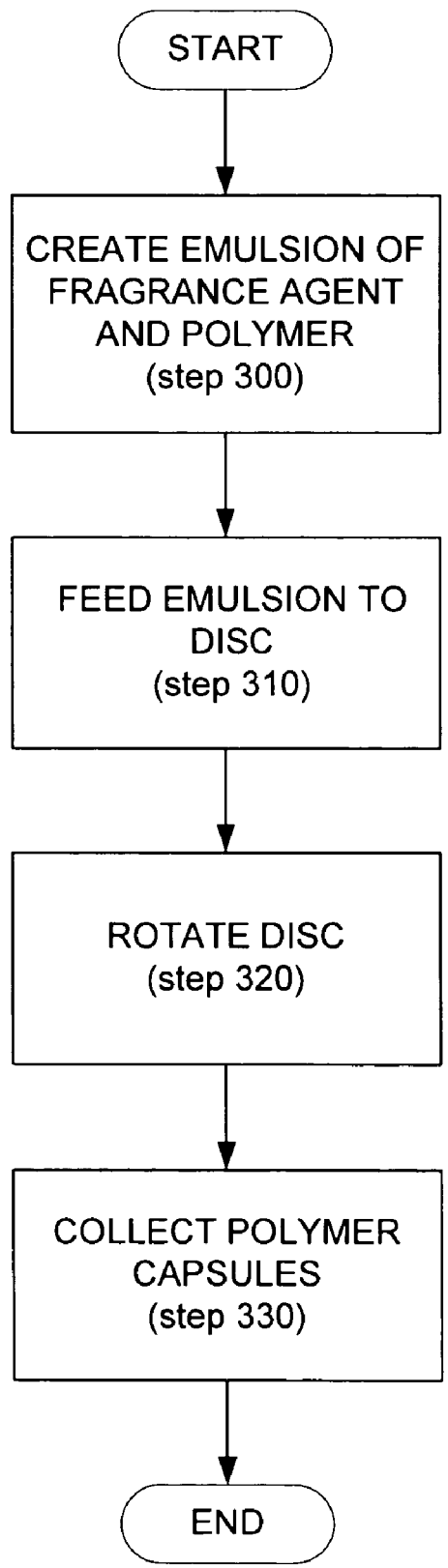
FIG. 3 is a simple block diagram illustrating a method of forming a fragrant polymer configured to be used in a growing medium, according to one exemplary embodiment.

In another exemplary embodiment, illustrated in FIG. 3, the microencapsulation technique used to form the fragrant polymer capsules includes a spinning disc process. According to the exemplary method illustrated in FIG. 3, an emulsion or suspension containing the fragrance agent is first prepared (step 300) with a solution or melt of the coating material, similar to the spray-drying process illustrated in FIGS. 1 and 2. Once prepared, the emulsion or suspension is fed to a disc surface (step 310) where it forms a thin wetted layer. Once the emulsion or suspension is fed to the disk surface, the disk is caused to rotate (step 320). During rotation of the disk, the thin layer of emulsion or suspension breaks up into airborne droplets due to surface tension forces that induce thermodynamic instabilities, resulting in spherical capsules that are then collected (step 330). According to one exemplary embodiment, the spinning disk process illustrated in FIG. 3 allows the use of a higher viscosity shell material and allows higher loading of the fragrance ingredient in the shell. A higher viscosity shell material may be used because the emulsion or suspension is not extruded through an orifice. Additionally, the spinning disk process also offers a broad range of particle sizes that may be formed with controlled distribution by varying the conditions of the rotating disk.

In yet another exemplary embodiment, the microencapsulation technique involves coextrusion encapsulation methods. According to this exemplary embodiment, the fragrant polymer capsules may be formed using stationary nozzle coextrusion, centrifugal coextrusion, or submerged nozzle coextrusion. All these processes involve concentric nozzles that pump the fragrance agent through an inner nozzle while the shell formulation is pumped through the annulus, allowing true "core-shell" morphologies. As the liquid stream exits the nozzle, local disturbances, such as induced vibration or gravitational, centrifugal, or drag force, control particle size. Typical microcapsules produced by coextrusion may range from approximately 100 micrometers to 6 mm.

The microencapsulation processes may further include chemical processes such as phase separation, gelation, and simple or complex coacervation. In one exemplary embodiment, the microencapsulation technique involves phase separation in which the fragrance agent is emulsified in a polymer solution and an antisolvent is subsequently added to induce the precipitation of the polymer around the fragrance agent. In another exemplary embodiment coacervation is used. In this technique microcapsule shells are formed by ionic interaction between two ionic polymers, typically a polyanion and a polycation. In another embodiment, gelation is used as the microencapsulation method and involves using a technique such as cooling, crosslinking, or a chemical reaction to form gelled microspheres or microcapsules.

It should be understood that the present system and methods may also include the use of any other microencapsulation technique known to those of skill in the art. Examples of these methods include, but are not limited to, vibrating nozzle, pan coating, fluid bed, spray coating, interfacial polymerization, solvent evaporation, in situ polymerization, liposome, sol-gel methods, nanoencapsulation, and others.

The polymer encapsulates the fragrance agent, thereby protecting it until the release of the fragrance agent into the environment is induced. Many different mechanisms may trigger the release of the fragrance agent to the environment. In one exemplary embodiment, the polymer is configured to release the fragrance agent through micropores created in the surface of the polymer when the addition of water causes the polymer to swell to a larger size. Release of the fragrance agent in the presence of water may be further facilitated by using hydrophobic fragrance agents that are repelled by absorbed water.

In an alternative exemplary embodiment, the polymer capsule is configured to release the fragrance agent by dissolving in the presence of water. Other release mechanisms that may be used to systematically release the fragrance agent include, but are in no way limited to, mechanical polymer rupture, thermal release, permeation, dissolution, delayed and targeted release, pH and osmotic release, photolytic release, biodegradation, and other release methods known to those of skill in the art.

Polymers that have a high capacity for absorbing water may also help ensure a higher yield and faster germination of a plant potted in the growing medium containing the fragrant polymer since they provide a constant source of water, even in periods of drought. Potassium-based polymers also provide the beneficial nutrient potassium to help in plant development. According to one exemplary embodiment, water absorbent polymers are used in potting soil, allowing them to absorb up to hundreds of times their weight in water and turn into a gel. The water absorbing polymers remain in this state until the plant extracts more water from the gel. These polymers are thus able to provide a plant with a readily available supply of water, even through great periods of neglect by a home owner. Water absorbent polymers can also improve the structure of soil through swelling and water release. Since the gel absorbs and releases water, it expands and contracts, thereby increasing air spaces in the soil, which the plant roots need to exchange oxygen and carbon dioxide. These and other beneficial characteristics may be provided in addition to the systematic release of a fragrance from the polymer.

Figure 4:
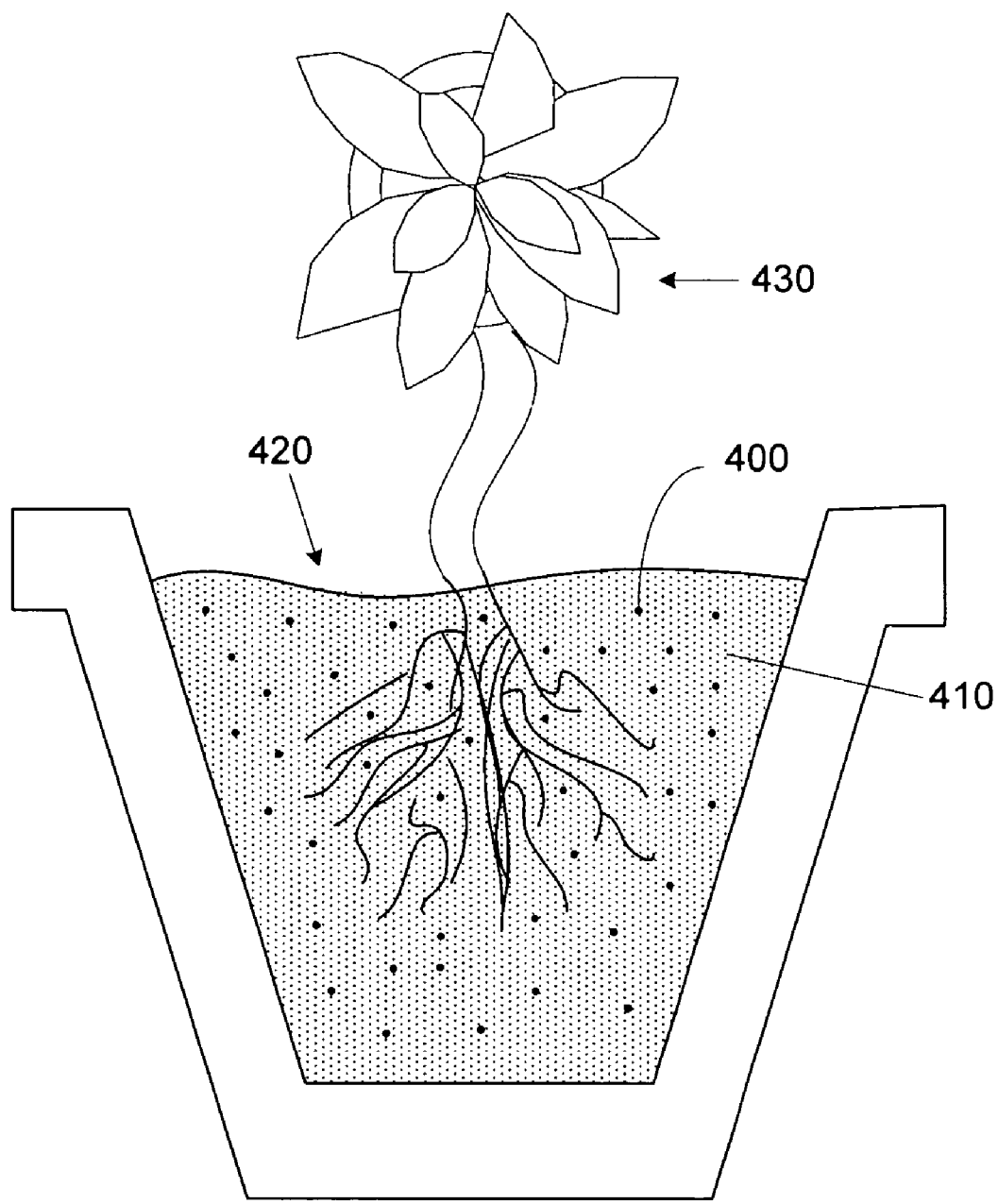
FIG. 4 is a cross-sectional side view illustrating a fragrant potting soil containing a fragrant polymer and its method of use, according to one exemplary embodiment.

FIG. 4 illustrates one exemplary embodiment of incorporating the fragrant polymer (400) in a growing medium. As illustrated in FIG. 4, fragrant polymers (400) are added to a potting medium (410) to make a fragrant potting soil (420). The fragrant soil (420) emits a pleasant aroma when the fragrance agent is released from fragrant polymers (400). Using this soil (420) provides a discrete and hassle-free method for eliminating odors and filling a room with a pleasant aroma while also providing watering and nutritional benefits to the plant (430).

Suitable potting media (410) may include any natural, soilless, and/or organic ingredients, which include, but are not limited to vermiculite, perlite, sand, silt, peat, charcoal, loam, fertilizer, compost, humus, manure, bone meal, blood meal, alfalfa meal, cottonseed meal, crab meal, feather meal, fish meal, soybean meal, kelp meal, granite meal, greensand, bat guano, seabird guano, colloidal phosphate, rock phosphate, wood ash, worm castings, ground limestone, pine bark, spaghnum peat moss, coir, alfalfa, kenaf, sawdust, ground newspaper, clay, leaf mold, and other organic ingredients known to those of skill in the art.

The potting soil (420) may comprise any mixture or blend of the above potting media (410). The specific blend used in each application usually depends on the type of plant, the environment surrounding the plant, and the climate, as well as other factors known to those of skill in the art. Generally, the potting soil (420) comprises from about 10% to about 20% by weight fragrant polymer, according to one exemplary embodiment.

In one embodiment, the fragrant potting soil (420) is loose to facilitate planting and shoveling of the soil. Loose soil also maintains a higher oxygen content in the soil and allows easier transport of oxygen and carbon dioxide through the soil. In another embodiment the potting soil (420) is compressed to lessen the volume and facilitate transportation of the soil.

According to one alternative embodiment, the fragrant polymers (400) may be packaged and distributed independently of the potting media (410). According to this exemplary embodiment, the fragrant polymers (400) may be independently distributed to be added to new potting media (410), or alternatively to be added to existing potting media as a refresher or aroma enhancer for old and/or depleted potting media.

In yet another alternative embodiment, the fragrant polymers (400) may include a fragrant agent designed to enhance a person's mood. According to this exemplary embodiment, the fragrant polymer (400) may include a fragrance agent configured to affect the mood and behavior of a person, similar to aromatherapy. The fragrance agent may include, but is in no way limited to, rosewood, ylang ylang, and rose to create an amorous mood; orange, spearmint, tea tree, an lemon to induce a fresh and bright feeling; peppermint, eucalyptus, and lavender to increase power and activity level; rosemary, lavender, eucalyptus, and ginger for increased energy; ylang ylang, cedar wood, and grapefruit for internal body balance; bergamot, chamomile, and lavender for serenity and tranquility; or any combination thereof. Further, grapefruit and clary may be used as a fragrance agent to stimulate endorphin production and lavender and marjoram may be combined and used as a fragrance agent to stimulate serotonin levels.

The preceding description has been presented only to illustrate and describe the present method and products. It is not intended to be exhaustive or to limit the disclosure to any precise form disclosed. Many modifications and variations are possible in light of the above teaching. It is intended that the scope of the present system and method be defined by the following claims.

What is claimed is:

1. A fragrant potting soil, comprising:
   a potting medium; and
   a fragrant polymer interspersed in said potting medium, wherein said fragrant polymer includes a water absorbent acrylic polymer and a fragrance agent microencapsulated in said water absorbent acrylic polymer.

2. The potting soil of claim 1, wherein said fragrant polymer comprises from about 10% to about 20% by weight of said potting soil.

3. The potting soil of claim 1, wherein said water absorbent polymer is configured to predictably release said fragrance agent.

4. The potting soil of claim 3, wherein said polymer is configured to release said fragrance agent by dissolution or swelling of said polymer in the presence of water.

5. The potting soil of claim 3, wherein said fragrance agent is configured to emit an aroma when released.

6. The potting soil of claim 1, wherein said fragrant polymer comprises at least one of an acrylamide potassium-acrylate copolymer or an acrylamide sodium-acrylate copolymer.

7. The potting soil of claim 1, wherein said fragrance agent comprises at least one of an essential oil, a fixed oil, a resin, a resinoid, an oleoresin, an absolute fragrance chemical, a concrete fragrance chemical, or a floral water.

8. The potting soil of claim 1, wherein said fragrance agent comprises at least one of citronella, a pesticide, or an insecticide.

9. A method of making a fragrant potting soil, comprising:
   adding a fragrant polymer including a fragrance agent to a potting medium;
   wherein said fragrant polymer is configured to systematically release said fragrance agent.

10. A method of making a fragrant potting soil, comprising: adding a fragrant polymer including a fragrance agent to a potting medium;
    wherein said fragrant polymer includes a water absorbent acrylic polymer and a fragrance agent microencapsulated in said water absorbent acrylic polymer; and
    wherein said fragrance polymer is configured to systematically release said fragrance agent.

11. The method of claim 10, wherein said fragrant polymer is formed by microencapsulated.

12. The method of claim 11, wherein said microencapsulation comprises one of spray drying encapsulation, coacervation encapsulation, or ecoextrusion encapsulation.

* * * * *